(12) United States Patent
Hong et al.

(10) Patent No.: US 9,046,498 B2
(45) Date of Patent: Jun. 2, 2015

(54) BOARD INSPECTION APPARATUS USING MULTIPLE CAMERAS

(75) Inventors: Jong-Kyu Hong, Gwangju-si (KR); Moon-Young Jeon, Seoul (KR); Hong-Min Kim, Seoul (KR); Jung Hur, Bucheon-si (KR); Sang-Kyu Yun, Chungju-si (KR)

(73) Assignee: KOH YOUNG TECHNOLOGY INC., Seoul (KR)

(*) Notice: Subject to any disclaimer, the term of this patent is extended or adjusted under 35 U.S.C. 154(b) by 321 days.

(21) Appl. No.: 13/522,673

(22) PCT Filed: Jan. 18, 2011

(86) PCT No.: PCT/KR2011/000343
§ 371 (c)(1),
(2), (4) Date: Jul. 17, 2012

(87) PCT Pub. No.: WO2011/087337
PCT Pub. Date: Jul. 21, 2011

(65) Prior Publication Data
US 2012/0287264 A1 Nov. 15, 2012

(30) Foreign Application Priority Data
Jan. 18, 2010 (KR) .................. 10-2010-0004398

(51) Int. Cl.
*H04N 7/18* (2006.01)
*G01N 21/95* (2006.01)

(52) U.S. Cl.
CPC .................. *G01N 21/9501* (2013.01)

(58) Field of Classification Search
USPC ........ 348/125–131, 85–87, 92; 382/145, 147, 382/149; 700/117, 121; 356/237.1, 239.7, 356/237.2
See application file for complete search history.

(56) References Cited

U.S. PATENT DOCUMENTS 5,495,337 A * 2/1996 Goshorn et al. ............... 356/601
5,880,772 A * 3/1999 Kalnajs et al. ................. 348/87
(Continued)

FOREIGN PATENT DOCUMENTS

CN 1715890 1/2006
DE 31 22 712 3/1982
(Continued)

OTHER PUBLICATIONS

Written Opinion of the International Searching Authority for International Application No. PCT/KR2011/000343, dated Sep. 30, 2011.
(Continued)

*Primary Examiner* — Victor Kostak
(74) *Attorney, Agent, or Firm* — Kile Park Reed & Houtteman PLLC (57) ABSTRACT

An apparatus for inspecting a board is shown. The board inspection apparatus includes at least one illuminating module, an imaging lens, a first beam splitter, a first camera, and a second camera. The illuminating module provides light to an inspection board and the imaging lens transmits a light reflected from the inspection board. The first beam splitter transmits a portion of the light transmitted from the imaging lens and reflects the rest of the transmitted light. The first camera image-captures by receiving the light that transmits the first beam, and the second camera image-captures by receiving the light reflected from the first beam splitter. Therefore, by using one imaging lens to inspect the inspection board, the decrease in accuracy caused by the different optical axis or magnification may be prevented.

12 Claims, 5 Drawing Sheets

(56) References Cited

U.S. PATENT DOCUMENTS

| | | | |
|---|---|---|---|
| 6,529,624 B1 * | 3/2003 | Kim | 382/150 |
| 8,008,641 B2 * | 8/2011 | Harris et al. | 250/559.41 |
| 2002/0027654 A1 * | 3/2002 | Owen et al. | 356/237.5 |
| 2005/0073590 A1 | 4/2005 | Mamiya | |
| 2008/0174691 A1 * | 7/2008 | Polidor et al. | 348/348 |
| 2009/0279079 A1 | 11/2009 | Shibata et al. | |
| 2010/0295938 A1 * | 11/2010 | Hahn et al. | 348/126 |

FOREIGN PATENT DOCUMENTS

| | | |
|---|---|---|
| JP | 06-066521 | 3/1994 |
| JP | 2001-194116 | 7/2001 |
| JP | 2001-249013 | 9/2001 |
| JP | 2002-048523 | 2/2002 |
| JP | 2002-122416 | 4/2002 |
| JP | 2006-162462 | 6/2006 |
| JP | 2009-257903 A | 11/2009 |
| KR | 10-2006-0000984 A | 1/2006 |
| KR | 10-2007-0120895 A | 12/2007 |

OTHER PUBLICATIONS

International Search Report of International Application No. PCT/KR2011/000343, dated Aug. 30, 2011.

* cited by examiner

BOARD INSPECTION APPARATUS USING MULTIPLE CAMERAS

TECHNICAL FIELD

The present invention relates to an apparatus for inspecting a board, and more particularly to an apparatus for inspecting a three dimensional shape of the board surface.

BACKGROUND ART

An apparatus for inspecting a three dimensional shape of a board surface has an illuminating module that provides light to the inspection object and an image-capture module that image-captures the reflected light from the inspection object, where the image-capture module has an imaging lens that transmits a light that is reflected from the inspection object and a camera that image-captures a light that transmits the imaging lens.

Recently, the size of the inspection object is becoming larger, however, comparing to the size of the inspection object, the image-capture area is becoming relatively smaller. As a result, to correspond with size of the inspection object, the latest image-capture module of the board inspection apparatus has a plurality of cameras and a plurality of imaging lenses that correspond with the cameras.

However, when inspecting the inspection object through the plurality of imaging lenses, different optical axis between the imaging lenses, different magnification between the imaging lenses, different distance between the imaging lenses and the inspection board, etc., may cause a distortion to occur between the images that are image-captured by the cameras, causing the inspection accuracy of the inspection board to decrease. Also, a complex algorithm may be necessary to compound a single integrated image that compensates a distortion of the image-captured images from the cameras.

DETAILED DESCRIPTION OF THE INVENTION

Objects of the Invention

Therefore, the present invention is to solve the above-described problem, the object of the present invention is to improve the inspection accuracy and to simplify the algorithm, and further providing a board inspection apparatus for inspecting larger areas. Moreover, regarding to a structure using multiple cameras, the size of the inspection apparatus may be reduced.

Technical Solution

The first exemplary embodiment of the board inspection apparatus includes at least one illuminating module, an imaging lens, a first beam splitter, a first camera and a second camera.

The illuminating module provides light to an inspection board and the imaging lens transmits a light reflected from the inspection board. The first beam splitter transmits a portion of the light transmitted from the imaging lens and reflects the rest of the transmitted light. The first camera image-captures by receiving the light that transmits the first beam splitter (hereinafter, referred to as "transmission light"), and the second camera image-captures by receiving the light reflected from the first beam splitter (hereinafter, referred to as "reflection light").

The first beam splitter may have a first reflective plane that the light is provided from the imaging lens, and transmits a portion of the provided light and reflects the rest of the provided light. The first reflective plane and a reference plane of the imaging lens may form a predetermined angle, and the first camera and the second camera may image-capture different areas of the inspection board. The first camera and the second camera may be disposed in different directions. The first reflective plane may transmit 50% and reflect 50% of the light provided from the imaging lens.

A centerline of an image-capture element of the first camera and a centerline of the imaging lens may be disposed to not to match with each other. In this case, a relationship may be satisfied: $i \geq 2b$, where $i$ is a width of the image-capture element of the first camera and $b$ is a horizontal distance between the center of the image-capture element of the first camera and the center of the imaging lens. In addition, a first area that is measured by the first camera and a second area that is measured by the second camera may have at least a partial overlap area.

The board inspection apparatus may further include a second beam splitter and a third camera. The second beam splitter is disposed between the first beam splitter and first camera, and provides the first camera with the transmitted portion of the transmission light and reflects the rest of the transmission light. The third camera image-captures by receiving the light reflected from the second beam splitter. The second beam splitter may have a second reflective plane that transmits a portion of the transmission light and reflects the rest of the transmission light.

In addition, the board inspection apparatus may further include a third beam splitter and a fourth camera. The third beam splitter is disposed between the first beam splitter and the reflection light camera, and provides the second camera with the transmitted portion of the reflection light and reflects the rest of the reflection light. The fourth camera image-captures by receiving the light reflected from the third beam splitter. In this case the third beam splitter may have a third reflective plane that transmits a portion of the reflection light and reflects the rest of the reflection light, and the third reflective plane and a reference plane of the imaging lens may form a predetermined angle.

Advantageous Effects

According to the board inspection apparatus, as the first beam splitter divides the light reflected from the inspection apparatus into two parts, and the divided reflected light is each provided to the two cameras, it is possible to expand the measuring area using one imaging lens. Therefore, different optical axis between the imaging lenses, the different magnification between the imaging lenses, or the different distance between the imaging lenses and the inspection board etc., which causes the inspection accuracy of the inspection board to decrease may be prevented, and the algorithm that combines images into a single integrated image using two cameras to image-capture the images may be more simpler. Furthermore, the volume of the inspection apparatus may be reduced by disposing multiple cameras in different directions.

However, when inspecting the inspection object through the plurality of imaging lenses, different optical axis between the imaging lenses, different magnification between the imaging lenses, different distance between the imaging lenses and the inspection board, etc., may cause a distortion to occur between the images that are image-captured by the cameras, causing the inspection accuracy of the inspection board to decrease. Also, a complex algorithm may be necessary to compound a single integrated image that compensates a distortion of the image-captured images from the cameras.

| Brief description of the drawing number | |
|---|---|
| 10: inspection board | 100: illuminating module |
| 200: imaging lens | 210: reference plane |
| 310: first beam splitter | 312: first reflective plane |
| 312a: first symmetry plane | 320: second beam splitter |
| 322: second reflective plane | 322a: second symmetry plane |
| 330: third beam splitter | 332: third reflective plane |
| 332a: third symmetry plane | 410: first camera |
| 420: second camera | 430: third camera |
| 440: fourth camera | |

EMBODIMENTS OF THE INVENTION

The invention is described more fully hereinafter with reference to the accompanying drawings, in which exemplary embodiments of the invention are shown.

However, this invention may be embodied in many different forms and should not be construed as limited to the embodiments set forth herein. Numerical terms such as "one", "two", etc. may be used as cardinal numbers to indicate various structural elements, however, the structural elements should not be limited by the terms. The terms are only used to distinguish one structural element from another structural element. For example, a first structural element may be named as second structural element if the right is not beyond the scope, the same applies to the second structural element that may be named as the first structural element.

The terms used in the present application are only to explain the specific embodiment and is not intended to limit the present invention. The terms "a", "an" and "the" mean "one or more" unless expressly specified otherwise. The terms "including", "comprising", etc., are to designate features, numbers, processes, structural elements, parts, and combined component of the application, and should be understood that it does not exclude one or more different features, numbers, processes, structural elements, parts, combined component.

The invention is described more fully hereinafter with reference to the accompanying drawings, in which exemplary embodiments of the invention are shown.

<Embodiment 1>

Figure 1:
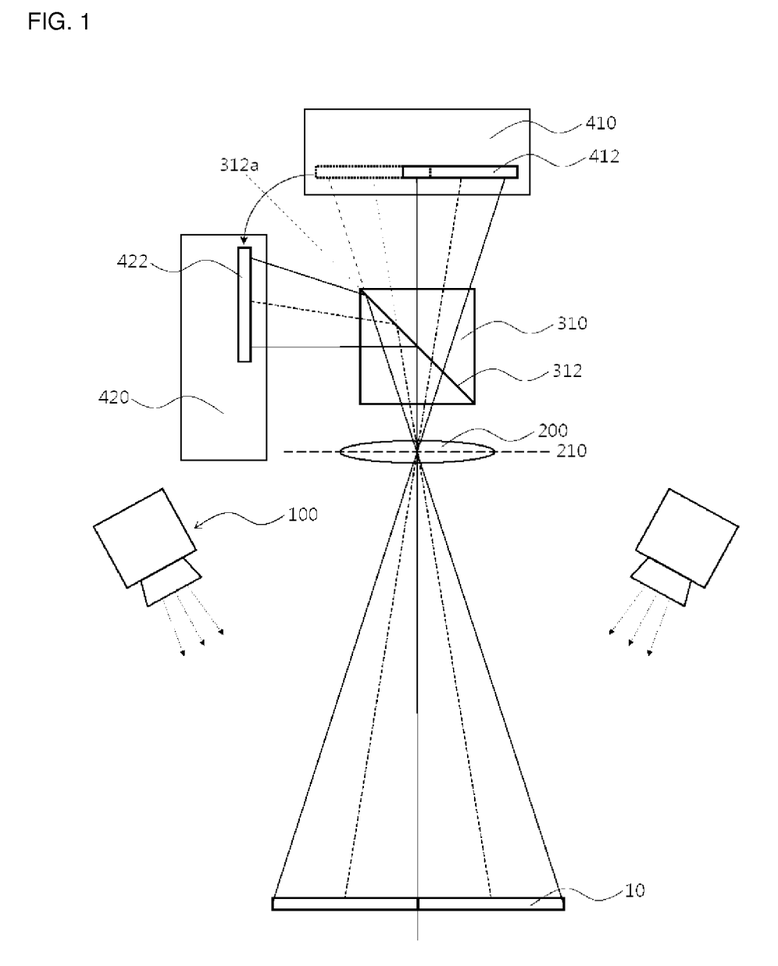
FIG. 1 is a sectional view illustrating a board inspection apparatus according to a first embodiment of the present invention.
Figure 2:
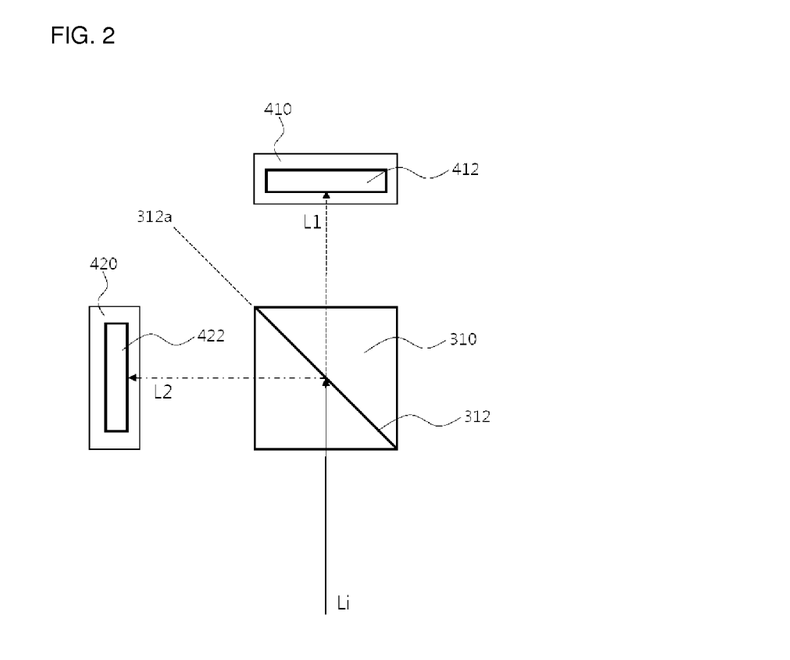
FIG. 2 is a conceptual sectional view illustrating a beam splitter and a camera of the board inspection apparatus illustrated in FIG. 1.
Figure 3:
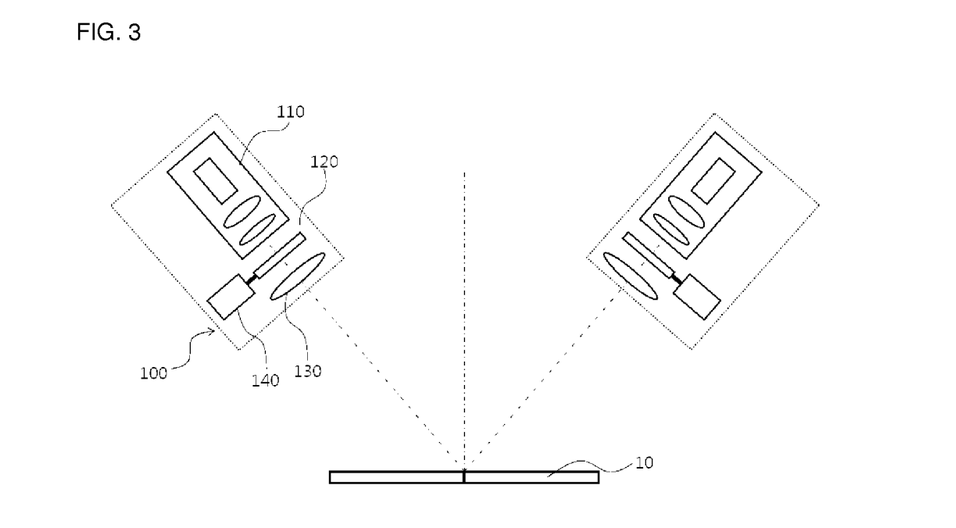
FIG. 3 is a magnified view illustrating an illuminating module of the board inspection apparatus illustrated in FIG. 1.

FIG. 1 is a sectional drawing showing a board inspection apparatus according to a first embodiment of the present invention, FIG. 2 is a conceptual sectional drawing of a beam splitter and a camera of the board inspection apparatus illustrated in FIG. 1, and FIG. 3 is a magnified drawing of an illuminating module of the board inspection apparatus illustrated in FIG. 1.

Referring to FIGS. 1 to 3, a board inspection apparatus according to the present embodiment corresponds to an apparatus for inspecting three dimensional shape of the surface of the inspection board that is disposed on a stage (not shown), which includes at least one illuminating module 100, an imaging lens 200, a first beam splitter 310, a first camera 410, a second camera 420 and a controlling system (not shown).

The illuminating module 100 may include an illuminating unit 110, a lattice unit 120, projection lens 130, and a lattice transfer unit 140. The illuminating unit 110 may include a light source and at least one lens to emit light, and the lattice unit 120 may be disposed below the illuminating unit 110 to change the light, which is emitted from the illuminating unit 110, into a lattice pattern light. The projection lens 130 is disposed in a lower part of the lattice unit 120 and transmits the lattice-shaped pattern light that is sent from the lattice unit 120. The lattice transfer unit 140 may move the lattice unit 120 in a predetermined stroke at a regular pitch.

The number of the illuminating module 100 may be 2, 3, 4, or more, for example, if the number of the illuminating module 100 is 4, the illuminating module 100 may be disposed at each vertex of the square. In this case, the center of the inspection board 10 may preferably substantially match with the center of the square.

The imaging lens 200 transmits the lattice-shaped pattern light reflected from the inspection board 10 and provides it to the first beam splitter 310. The reference plane 210 of the imaging lens 200 may be disposed to be practically parallel with the inspection board 10, and also the center of the imaging lens 200 may practically match with the center of the inspection board 10. In this case, for example, the center of the imaging lens 200 may practically match with the optical axis of the imaging lens 200 that is practically parallel with the normal direction of the reference plane 210 of the imaging lens 200.

The first beam splitter 310 may transmit a portion of the light transmitted from the imaging lens 200 and reflects the rest of the transmitted light. Specifically, the first beam splitter 310 includes a first reflective plane 312 that the light is provided from the imaging lens that transmits a portion of the provided light and reflects the rest of the provided light. In this case, the first reflective plane 312 and a reference plane 210 of the imaging lens 200 may form a predetermined angle, for example 45 degrees. Also, the first reflective plane 312 may transmit 50% and reflect 50% of the light provided from the imaging lens 200.

In the present embodiment, a light that transmits the imaging lens 200 is called an entering light (Li), the entering light (Li) that transmits the first beam splitter is called a transmission light (L1), and the entering light (Li) that is reflected from the first beam splitter 310 is called as a reflection light (L2).

The first camera 410 includes a first image-capture element 412 that is disposed in a location to receive the transmission light L1 that is sent from the first beam splitter 310, and may image-capture the transmission light L1. Furthermore, a second image-capture element 422 that is disposed in a location to receive the reflection light L2 that is sent from the first beam splitter 310, may image-capture the reflection light L2.

In this case, the first camera 410 and the second camera 420 may be either CCD camera or CMOS camera.

The first camera 410 and the second camera 420 may image-capture different areas of the inspection board 10. In other words, the first camera 410 and second camera 420 may at least image-capture a partial overlap area of the inspection board 10.

The first camera 410 and the second camera 420 may be disposed in different directions, and more specifically, may be symmetry disposed to a first symmetry plane 312*a* that is a virtual line extended from the first reflective plane 312. For example, one of the entering light (Li) that is placed on one part of the first beam splitter 310 may be provided to the first image-capture element 412 of the first camera 410 and may be image-captured, another entering light (Li) that is placed on the other part of the beam splitter 310 may be provided to the second image-capture element 422 of the second camera 420 and may be image-captured. Which means that the first image-capture element 412 image-captures the light placed in one part of the first beam splitter 310, and the second image-capture element 422 image-captures the light placed on the other part of the first beam splitter 310. As a result, the present embodiment of the board inspection apparatus may image-capture all areas of the entering light (Li) using the first image-capture element 412 and the second image-capture element 422.

The controlling system inspects the inspection board using the images that are image-captured by the image-capture module. For example, the controlling system may further include an image receiving part, a module controlling part, and a central controlling part.

The image receiving part may be electrically connected with the first camera 410 and the second camera 420, and may store the pattern images of the inspection board 10 that are provided by the first camera 410 and the second camera 420. The module controlling part may control and be connected with a stage that holds the inspection apparatus 100, the first camera 410, the second camera 420, and the illuminating module 100, and may include, for example, an illuminating controller that controls the illuminating unit, a lattice controller that controls the lattice transfer unit, and a stage controller that controls the stage. The central controlling part may control and be electrically connected with the image receiving part and the module controlling part, and may include an image processing board, a controlling board, and an interface board.

Again according to FIG. 3, when the lattice pattern light that is transmitted from one of the illuminating part of the multiple illuminating modules 100 is sent to the inspection apparatus 10, a lattice-shaped pattern image is formed on the inspection board 10. The lattice-shaped pattern image may include multiple lattice shapes, according to the present embodiment, the gap between the lattice shapes may have the same value regardless of the type of the lattice pattern light, however, the values may have different values regarding to the type of the lattice pattern light.

The lattice pattern light that is reflected from the inspection board 10 may form a plurality of pattern images using the first and second cameras 410 and 420. More specifically, N number of the lattice pattern light may be sent to the inspection board 10, for example moving 3 or 4 times sideways, to form N number of the pattern images.

Further continuing, the controlling system samples the N number brightness level of the each location in the X-Y coordinate system from the N number pattern images in each direction, and calculates a phase of the each direction, an average brightness, and a visibility. In this case, N-bucket algorism may be used to calculate a phase of the each direction, an average brightness, and a visibility.

Figure 4:
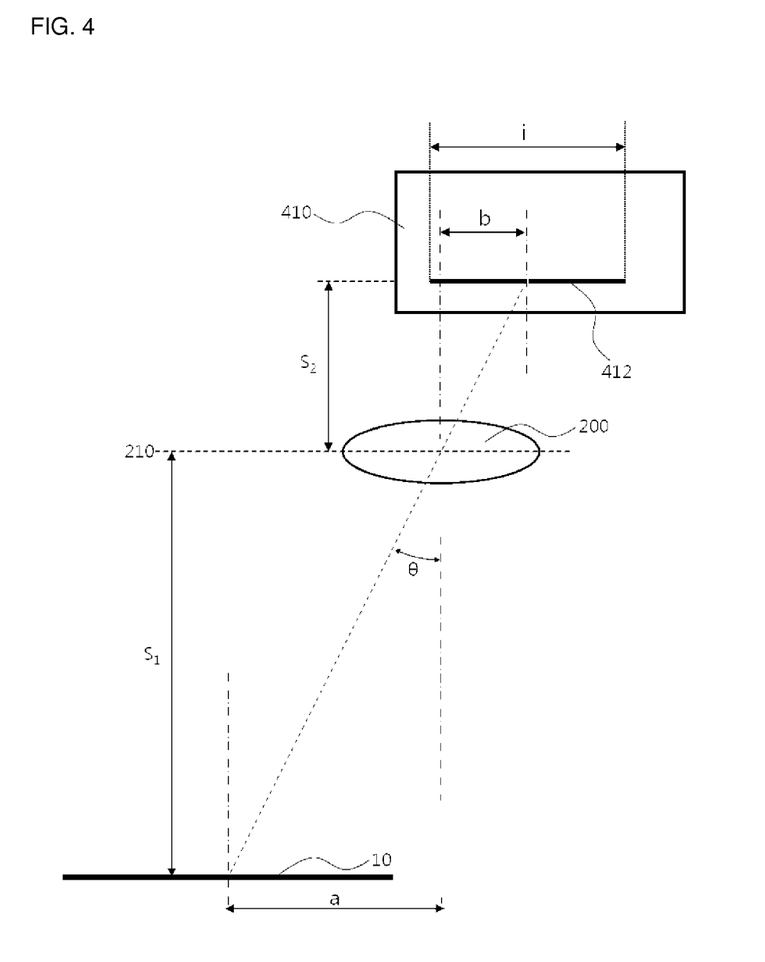
FIG. 4 is a drawing illustrating a relationship between an inspection apparatus, an imaging lens and a first camera of the inspection apparatus in FIG. 1.
Figure 5:
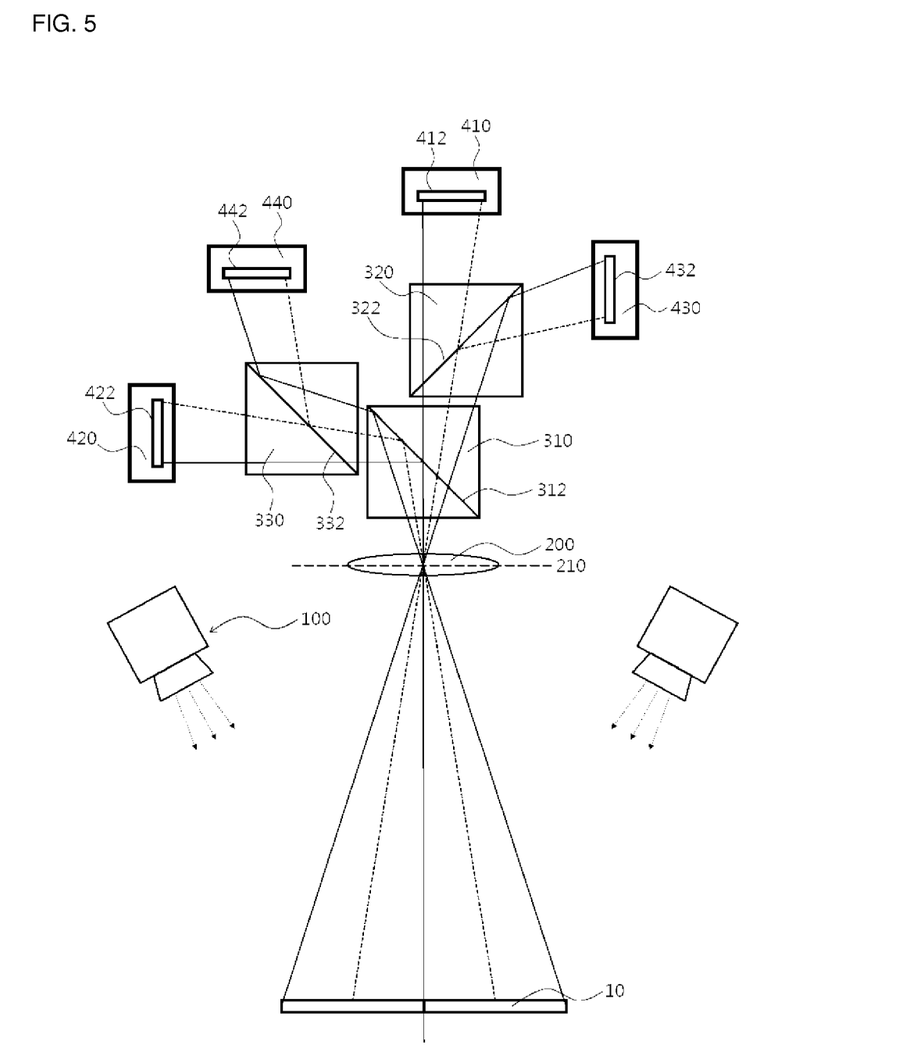
FIG. 5 is a sectional view illustrating a board inspection apparatus according to a second embodiment of the present invention.
Figure 6:
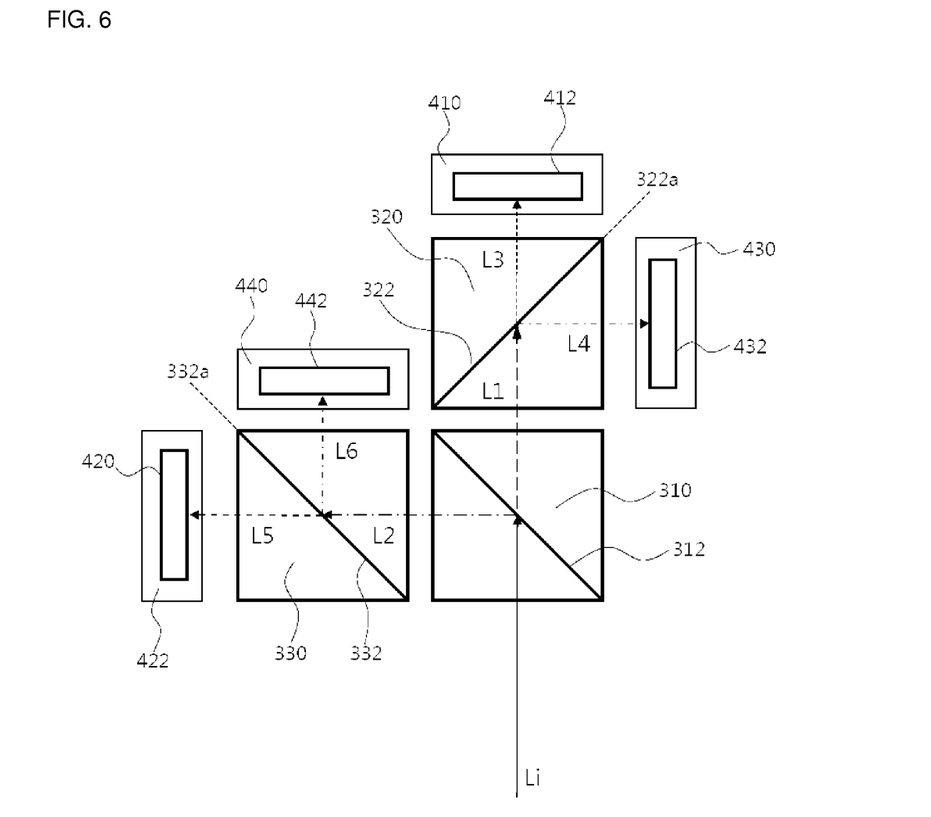
FIG. 6 is a conceptual sectional view illustrating a beam splitter and a camera of the board inspection apparatus illustrated in FIG. 5.

FIG. 4 is a drawing explaining a relationship between an inspection apparatus, an imaging lens and a first camera of the inspection apparatus in FIG. 1. In this case, the first beam splitter 310 is omitted in FIG. 4.

According to FIG. 4, a centerline of the first camera 410, i.e. a centerline of the first image-capture element 412, and a centerline of the imaging lens 200 may be disposed to not to match with each other, and a centerline of the inspection apparatus 10 and a centerline of the imaging lens 200 may be disposed to not to match with each other. For example, a centerline of the first image-capture element 412 and a centerline of the inspection apparatus 10 may be disposed on each side of a centerline of the imaging lens 200.

A relationship $1/S1+1/S2=1/F$ is established (F is a focal distance of the imaging lens 200), where a first separated distance S1 is a vertical distance between the inspection board 10 and the reference plane 210 of the imaging lens 200, and a second separated distance S2 is a vertical distance between the reference plane 210 of the imaging lens 200 and the first image-capture element 412. Furthermore, a relationship $a=S1 \cdot \tan(\theta)$, $b=S2 \cdot \tan(\theta)$ is established, where a is a horizontal distance between the centerline of the imaging lens 200 and the centerline of the inspection board, b is a horizontal distance between the centerline of imaging lens and the centerline of the first image-capture element 412, $\theta$ is an angle between a line that links a center of the inspection board 10 and a center of the first image-capture element 412, and a center of the imaging lens 200.

According to the present embodiment, a following relationship may be satisfied: $i \geq 2b$, where i is a width of the first image-capture element 412, in other words, a width that may be image-captured by the first image-capture element 412, and b is a horizontal distance between a center of the first image-capture element 412 and a center of the imaging lens 200. So to speak, when using one imaging lens 200 and a multiple camera to measure each area of the inspection board 10, the imaging lens 200 and multiple cameras should satisfy a relationship $i \geq 2b$, in order to measure the entire area of the inspection board 10. In this case, when the first image-capture element 412 overlaps with the center of the imaging lens 200 as shown in FIG. 3, a relationship $i \geq 2b$ is satisfied, and as a result, the area that the image-capture element of the cameras may image-capture may at least have a partial overlap area and measure the entire area of the inspection board 10.

Meanwhile, a relationship between the inspection board 10, the imaging lens 200, and the second camera is not described, however, except that the first beam splitter 310 provides light to the second camera 420, the relationship between the inspection board 10, the imaging lens 200, and a first camera are practically the same.

According to the present embodiment, the relationship between a first beam splitter 310, first camera 410, and a second camera 420 in FIG. 1 and FIG. 2 and the relationship between a second beam splitter 320, a first camera 410, and a third camera 430 in FIG. 3 and FIG. 4, are practically the same, and the relationship between a entering light Li, a transmission light L1, and a reflection light L2 in FIG. 1 and FIG. 2 and the relationship between a transmission light L1, transmitted-transmission light L3, and a transmitted-reflection light L4 in FIG. 3 and FIG. 4, are practically the same. Therefore, a description between the relationship between a second beam splitter 320, a first camera 410, and a third camera 430 in FIG. 3 and FIG. 4 and the relationship between an entering light L1, transmitted-transmission light L3, and a transmitted-reflection light L4 in FIG. 3 and FIG. 4, will be omitted.

The third beam splitter 330 is disposed between the first beam splitter 310 and the second camera 420, and provides the second camera 420 with a transmitted portion of the reflection light L2 and reflects the rest of the reflection light. In other words, the third beam splitter 330 includes a third reflective plane 332 that transmits a portion of the reflection light L2 and reflects the rest if the reflection light L2.

The third reflective plane 332 and the reference plane 210 of the imaging lens 200 may have a predetermined angle, such as approximately 45 degree. Furthermore, the third reflective plane 332 may transmit approximately 50% of the reflection light L2, and may reflect the rest, approximately 50%, of the reflection light. While in the present embodiment, a reflected-transmission light L5 is a reflection light L2 that transmits the third beam splitter 300, a reflected-reflection light L6 is a reflection light L2 that is reflected from the third beam splitter 330.

The fourth camera 440 is disposed on a location for providing the reflected-reflection light L6 that is sent from the third beam splitter 330, and includes a fourth image-capture element 442 that may image-capture the reflected-reflection light L6. The second camera 420 and the fourth camera 440 may be disposed at a symmetry position with respect to a third symmetry plane 332a that is a virtual extension plane from the third reflective plane 332.

In the present embodiment, the relationship between a first beam splitter 310, a first camera 310, and a second camera 420 in FIG. 1 and FIG. 2, and the relationship between a third beam splitter 330, a second camera 420, and a fourth camera 440 in FIG. 3 and FIG. 4, are practically the same, the relationship between an entering light Li, a transmission light L1, and a reflection light L2 in FIG. 1 and FIG. 2, and the relationship between a reflection light L2, a reflected-transmission light L5 and a reflected-reflection light L6 in FIG. 3 and FIG. 4, are practically the same.

Therefore, a description between the relationship between a third beam splitter 330, a second camera 420, and a fourth camera 440 in FIG. 3 and FIG. 4 and the relationship between an a reflection light L2, a reflected-transmission light L5 and a reflected-reflection light L6 in FIG. 3 and FIG. 4, will be omitted.

In the present embodiment, the board inspection apparatus is described to have three beam splitters (310, 320, 330) and four cameras (410, 420, 430, 440), however, in some cases, the number of the beam splitter and the number of the camera may be changed. In other words, when an additional beam splitter is be disposed between one of the beam splitter and one of the camera, an additional camera may be disposed to image-capture the reflected light provided from the additional beam splitter, therefore the number of the beam splitter and the number of the camera may further increase.

According to the present embodiment, by increasing the number of the beam splitter to diverse the split path of the light transmitted from the imaging lens 200, the image-capture area that uses one imaging lens may increase.

The detailed description of the present invention is described with regard to the preferable embodiment of the present invention, however, a person skilled in the art may amend or modify the present invention within the spirit or scope in the following claim of the present invention.

What is claimed is:

1. A board inspection apparatus comprising:
    at least one illuminating module that provides a pattern light to an inspection board;
    an imaging lens that transmits the pattern light reflected from the inspection board;
    a first beam splitter that transmits a portion of the pattern light transmitted from the imaging lens and reflects the rest of the transmitted pattern light;
    a first camera that image-captures by receiving the pattern light which is transmitted by the first beam splitter (hereinafter, referred to as "transmission light"); and
    a second camera that image-captures by receiving the pattern light reflected from the first beam splitter (hereinafter, referred to as "reflection light"), wherein a centerline of an image capture element of the first camera is offset from a centerline of the imaging lens.

2. The board inspection apparatus of claim 1, wherein the first beam splitter comprises:
    a first reflective plane which the pattern light is provided from the imaging lens, transmits a portion of the provided pattern light and reflects the rest of the provided pattern light.

3. The board inspection apparatus of claim 2, wherein the first reflective plane and a reference plane of the imaging lens forms a predetermined angle.

4. The board inspection apparatus of claim 3, wherein the first camera and the second camera image-captures different areas of the inspection board.

5. The board inspection apparatus of claim 4, wherein the first camera and the second camera are disposed in different directions.

6. The board inspection apparatus of claim 2, wherein the first reflective plane transmits 50% and reflects 50% of the pattern light provided from the imaging lens.

7. The board inspection apparatus of claim 1, wherein a following relationship
    is satisfied: $i > 2b$, where i is a width of the image-capture element of the first camera and b is a horizontal distance between the center of the image-capture element of the first camera and the center of the imaging lens.

8. The board inspection apparatus of claim 1, wherein a first area that is measured by the first camera and a second area that is measured by the second camera have at least a partial overlap area.

9. The board inspection apparatus of claim 1, further comprising:
    a second beam splitter disposed between the first beam splitter and the first camera, and provides the first camera with the transmitted portion of the transmission light and reflects the rest of the transmission light; and
    a third camera that image-captures by receiving the light reflected from the second beam splitter.

10. The board inspection apparatus of claim 9, wherein the second beam splitter comprises:
    a second reflective plane that transmits a portion of the transmission light and reflects the rest of the transmission light,
    the second reflective plane and a reference plane of the imaging lens forms a predetermined angle.

11. The board inspection apparatus of claim 9, further comprising:
    a third beam splitter disposed between the first beam splitter and the reflection light camera, and provides the second camera with the transmitted portion of the reflection light and reflects the rest of the reflection light; and
    a fourth camera that image-captures by receiving the light reflected from the third beam splitter.

12. The board inspection apparatus of claim 11, wherein the third beam splitter comprises:

a third reflective plane that transmits a portion of the reflection light and reflects the rest of the reflection light, and the third reflective plane and a reference plane of the imaging lens forms a predetermined angle.

* * * * *